(12) United States Patent
Tujkovic

(10) Patent No.: US 10,212,614 B2
(45) Date of Patent: Feb. 19, 2019

(54) IGNITING NETWORK NODES IN A MULTI-HOP WIRELESS NETWORK

(71) Applicant: Facebook, Inc., Menlo Park, CA (US)

(72) Inventor: Djordje Tujkovic, Mountain View, CA (US)

(73) Assignee: Facebook, Inc., Menlo Park, CA (US)

( * ) Notice: Subject to any disclaimer, the term of this patent is extended or adjusted under 35 U.S.C. 154(b) by 75 days.

(21) Appl. No.: 15/392,882

(22) Filed: Dec. 28, 2016

(65) Prior Publication Data

US 2017/0195899 A1    Jul. 6, 2017

Related U.S. Application Data

(60) Provisional application No. 62/274,115, filed on Dec. 31, 2015.

(51) Int. Cl.
*H04W 24/02* (2009.01)
*H04B 7/06* (2006.01)
*H04L 12/24* (2006.01)
*H04W 72/04* (2009.01)
*A61K 38/17* (2006.01)

(52) U.S. Cl.
CPC ......... *H04W 24/02* (2013.01); *A61K 38/1754* (2013.01); *H04B 7/0617* (2013.01); *H04L 41/0806* (2013.01); *H04W 72/046* (2013.01)

(58) Field of Classification Search
CPC .. H04B 7/0617; H04L 41/0806; H04W 24/02; H04W 72/046
See application file for complete search history.

(56) References Cited

U.S. PATENT DOCUMENTS

| | | | |
|---|---|---|---|
| 2003/0100343 A1* | 5/2003 | Zourntos | H04W 52/241 455/562.1 |
| 2016/0021597 A1* | 1/2016 | Hart | H04W 40/06 370/329 |
| 2016/0381596 A1* | 12/2016 | Hu | H04B 7/0617 370/236 |
| 2017/0195899 A1* | 7/2017 | Tujkovic | A61K 38/1754 |

\* cited by examiner

*Primary Examiner* — Benjamin H Elliott, IV
(74) *Attorney, Agent, or Firm* — Baker Botts L.L.P.

(57) ABSTRACT

In one embodiment, a method includes, by each of one or more network nodes of a multi-hop wireless network that are configured as initiators: receiving from a central controller an address of a particular network node that is configured as a responder. Using the address and by adjusting beamforming weights, the initiator may transmit a message to establish a wireless connection with a particular network node that is configured as a responder. Each responder may adjust its beamforming to receive a message from one of the initiators addressed to the responder to establish a wireless connection with the responder. When the responder receives the message from the initiator addressed to the responder, the responder may respond to the initiator to establish a wireless connection with the initiator.

19 Claims, 7 Drawing Sheets

IGNITING NETWORK NODES IN A MULTI-HOP WIRELESS NETWORK

PRIORITY

This application claims the benefit, under 35 U.S.C. § 119(e), of U.S. Provisional Patent Application No. 62/274,115, filed 31 Dec. 2015, which is incorporated herein by reference.

TECHNICAL FIELD

This disclosure generally relates to wireless communication networks.

BACKGROUND

A multi-hop wireless network may facilitate the communication of data where wired communication is unavailable, impractical, or impossible. For example, a multi-hop wireless network may serve as a wireless backhaul network connecting a core or backbone network to one or more customer networks. A customer network may include customer equipment (CE)—such as Wi-Fi access points (APs), cellular base stations (such as femtocells), and related equipment or other CE—providing wireless or wired connectivity to one or more client devices. A client device may be a desktop or laptop computer, tablet, mobile telephone, appliance, or other client device.

A multi-hop wireless network may include multiple wirelessly interconnected network nodes. A wireless connection between two network nodes may be a hop, and data may be communicated wirelessly through the network from one edge to another along one or more network paths traversing series of network nodes and hops. All or some of the network nodes may be at fixed locations. For example, all or some of the network nodes may be affixed to street lamps, utility poles, other street furniture, or building exteriors. All or some of the network nodes may act as distribution nodes (DNs) or customer nodes (CNs). A DN may wirelessly communicate with CNs or other DNs to relay data through the network. One or more DNs may also communicate with one or more edge devices of a core or backbone network to connect the multi-hop wireless network to the core or backbone network. A CN may communicate with DNs and CEs to connect a customer network to the multi-hop wireless network.

SUMMARY OF PARTICULAR EMBODIMENTS

Particular embodiments involve installing and igniting one or more network nodes on a multi-hop wireless network. The network nodes may be installed at pre-identified locations or in an arbitrary manner. The network nodes may then be ignited. Ignition for a particular network node may occur when an antenna array of the particular network node establishes a wireless connection with another antenna array of a different network node. In particular embodiments, network ignition may involve using information and data that has been predetermined and loaded either directly onto a memory store in the network nodes themselves or on a central controller or other suitable computing device. The information and data may include settings regarding beamforming weights for one or more antenna arrays in each of the network nodes. The information and data may also include Global Positioning System (GPS) data, orientations of the network nodes and other information that may be useful in igniting the nodes. However, information about adjustments to make to beamforming weights, orientations, and other setting may be unavailable to the network nodes. This may inhibit the network nodes' ability to achieve a wireless connection with another network node in an efficient manner. When no such information is available, the network nodes may need to adjust the beamforming weights on their antenna arrays to scan or sweep the surrounding area for an other network node to establish a wireless connection. Once a wireless connection has been established, it may be assumed that the network nodes with wireless connections are operating in the steady state. During steady state operation, information and statistics about the operation of the network nodes may be recorded. Such information and statistics may include beamforming weights adjustments, GPS locations and orientation of one or more network nodes, and other information relating to how wireless connections are established between network nodes.

Re-ignition of one or more network nodes may be required for a variety of reasons (e.g. network node failure due to inclement weather or earthquakes, routine or planned maintenance, etc.). If re-ignition of one or more network nodes is required, the information and statistics recorded during the previous steady state operation may be used to more quickly form wireless connections between network nodes. The central ignition controller or network nodes themselves may have this information and statistics stored for use during re-ignition. The information and statistics may be used to quickly determine the beamforming weights adjustments needed to form a wireless connection. Using this prior knowledge gained from one or more previous steady state operations to re-ignite the network in a more efficient manner may be referred to as "warm start."

DESCRIPTION OF EXAMPLE EMBODIMENTS

Figure 1:
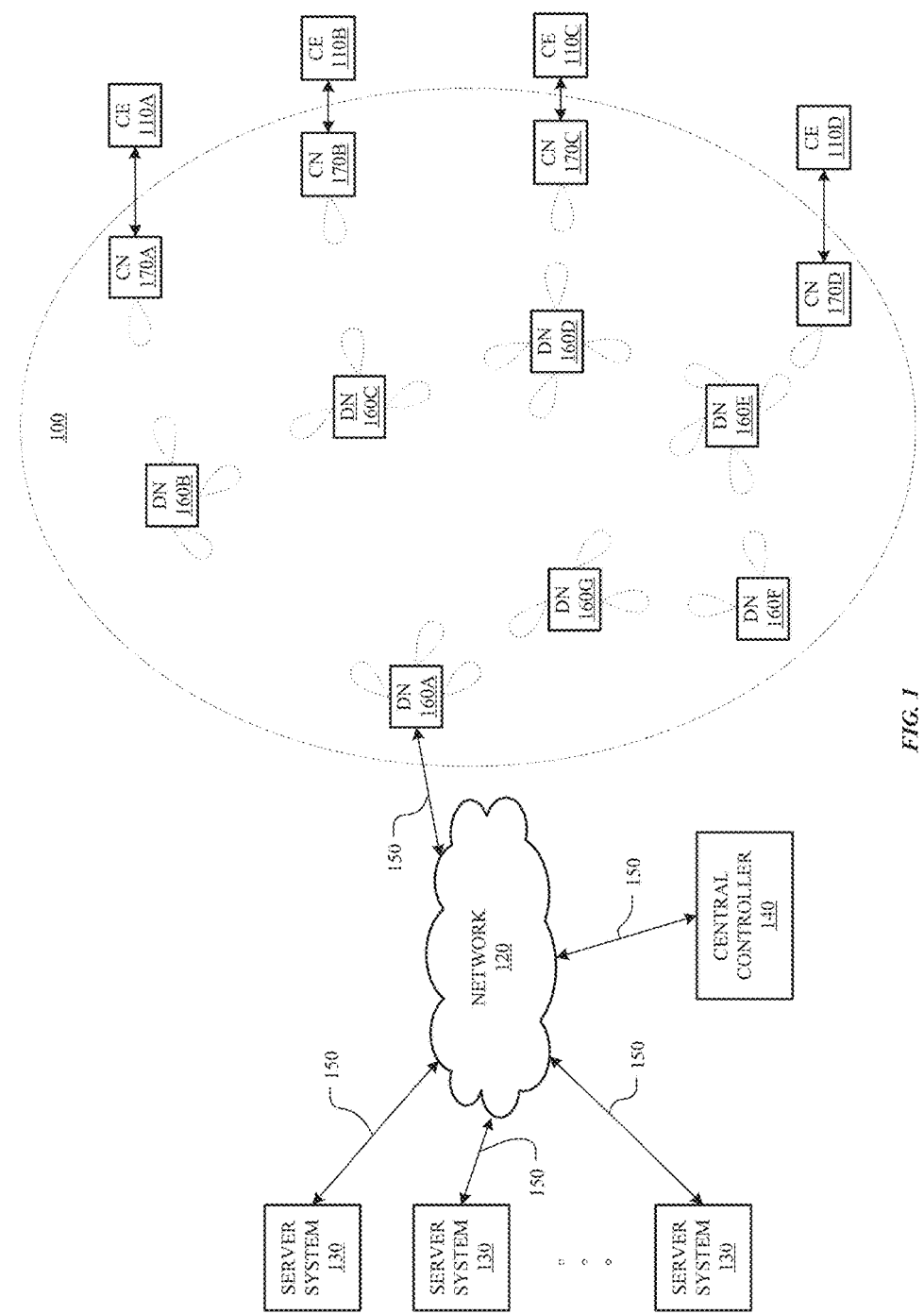
FIG. 1 illustrates an example multi-hop wireless network.

In particular embodiments, to install and ignite network nodes in a multi-hop wireless network, the physical locations where the network nodes will be installed are identified. The physical locations may be street furniture (such as lampposts), customized structures made specifically to house network nodes, or a combination of the two. The identification of the physical locations can be done in a systematic way with network-deployment tools. Such tools have several functions, such as (1) predicting which individual links need to be "ignited" (which can provide the initial trunking of the network topology); (2) computing GPS locations, heights, and azimuth/elevation tilts for optimal network deployment and performance; and (3) generating a deployment plan for the installer(s).

In particular embodiments, installation of a network node involves the following steps. First, the network node is placed at the planned deployment location (such as a particular lamppost or wall). Next, the network node is powered on and the firmware or the location-specific configuration parameters (such as an override Media Access Control (MAC) address) are loaded onto the network node. Next, dedicated firmware optionally acquires location, frequency, and timing and phase sync information from a GPS module connected to the network node. Next, using out-of-band signaling (e.g. 2G, 3G, or 4G mobile telecommunications), a central controller is optionally informed that the network node has been installed and provided with its GPS location. Next, dedicated firmware checks whether the network node has a connection to the central ignition controller through an in-band link. If yes, then the network node waits to be configured by the central ignition controller as an "initiator" or a "responder" in the ignition procedure. If no, then the network node automatically configures itself as a responder.

In particular embodiments, ignition of the network involves the following steps. First, the central controller sets each network node to initiator mode or responder mode. If a network node has an in-band connection to the central controller, then the network node sets the network node to initiator mode and triggers the initiator procedures in the network node. The initiator procedure may involve a beam-forming acquisition procedure in which an initiator and responder sweep beam-forming weights until a wireless connection is established between them. Next, the receipt MAC address for the initiator procedure is set to a value targeting a particular responder. This helps to ensure that other network nodes that are set to responder mode do not respond to the initiator and create multi-access interference with the target responder. If the target responder does not respond within a pre-determined amount of time, then the initiator sets the broadcast MAC for the recipient address in the initiator procedure, which allows un-ignited network nodes to respond to the ignitor initiator. When this happens, network nodes that have not yet been ignited may respond to the initiator procedure. Upon successful ignition, the responder is associated with the network at L2. Optionally, the link IP is provided to the network processor to establish an L3 connection to the responder.

In particular embodiments, there are three options to install the network in conjunction with igniting it. The first option is to do a full installation followed by a full ignition. This is accomplished by placing all the network nodes on the planned deployment locations in an arbitrary order throughout the deployment area. Then all the network nodes switch to responder mode after optional GPS acquisition. The second option is to install and ignite the network nodes on a link by link basis. This is accomplished by installing the network nodes one at a time and starting ignition on each node via the central controller. If the ignition of a link fails, the network node will be adjusted or re-oriented and ignition will be re-tried. The third option is to perform a combination of options one and two. In this case, installation and ignition is performed on subsets of network nodes, referred to as "subnets." Regardless of which option is chosen, the network is ignited in serial fashion, one hop at a time, because the network node in Initiator mode needs to have a connection to the Ignition controller. In particular embodiments, there is an exception to serial ignition: in the case of "warm-start re-ignition," re-ignition can be done in parallel based on data gathered during the steady state phase of the network.

In particular embodiments, a warm-start re-ignition occurs as follows. After the network (or subnets) have already operated in steady state, the network operation may need to return to the Ignition state for various reasons. For example, power outages could cause the network nodes to reset. Re-ignition of the network nodes can be done by a cold-start, or by a warm-start. Cold start involves re-ignition of the network from scratch, as if it never operated in that geographic area. This is not ideal. Warm start, on the other hand, uses knowledge and statistics gathered from the steady state phase to reduce time and increase the success rate of re-igniting the network. For example, the ignition controller can inform individual network nodes about the state information, which the network nodes can implement immediately upon resetting. This allows the network nodes to be ignited in parallel by defaulting to the last known good state.

FIG. 1 illustrates an example multi-hop wireless network 100. In the example of FIG. 1, multi-hop wireless network 100 connects CE 110 at customer premises (such as residences or places of businesses) to a core or backbone network 120 (which may include one or more portions of the Internet). Network 120 connects multi-hop wireless network 100 to one or more server systems 130. Network 120 may also connect central controller 140 to multi-hop wireless network 100. As described below, a connection between central controller 140 and a network node of multi-hop wireless network 100 may be an in-band connection or out-of-band connection. Links 150 may connect multi-hop wireless network 100, server systems 130, and central controller 140 to network 110. This disclosure contemplates any suitable links 150 for these connections. For example, one or more links 150 may include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links, where appropriate. In particular embodiments, one or more links 150 may each include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the PSTN, a 2G, 3G, or 4G mobile-telecommunications network, a satellite communications network, another link 150, or a combination of two or more such links 150, where appropriate. Links 150 are not necessarily the same throughout the network environment of FIG. 1. One link 150 may differ from another in one or more respects. Although the example of FIG. 1 is described and illustrated with a particular network environment including a particular number of particular systems and components arranged in a particular manner, this disclosure contemplates any suitable network environment including any suitable number of any suitable systems and components arranged in any suitable manner. For example, two or more of multi-hop wireless network 100, server systems 130, or central controller 140 may be connected to each other directly, bypassing network 120. As another example, two or more of multi-hop wireless network 100, server systems 130, or central controller 140 may be physically or logically co-located with each other in whole or in part.

A connection between central controller 140 and a network node of multi-hop wireless network 100 may be an in-band connection or out-of-band connection. An in-band connection between central controller 140 and a network node of multi-hop wireless network 100 is a connection that traverses network 120 and wireless network 100. An out-of-band connection between central controller 140 and a network node of multi-hop wireless network 100 is a connection that bypasses in whole or in part network 120 or multi-hop wireless network 100. For example, in FIG. 1, an in-band connection between central controller 140 and CN 170A may traverse the following: (1) link 150 between central controller 140 and network 120; (2) network 120; (3) link 150 between network 120 and DN 160A; (4) DN 160A; (5) a direct wireless connection between DN 160A and DN 160B; (5) DN 160B; and (6) a direct wireless connection between DN 160B and CN 170A. An out-of-band connection between central controller 140 and CN 170A may include one or more wireless connections between them through one or more portions of a 2G, 3G, or 4G mobile telecommunications network, bypassing one or more of the following: (1) link 150 between central controller 140 and network 120; (2) network 120; (3) link 150 between network 120 and DN 160A; or (4) multi-hop wireless network 100. Although this disclosure describes particular in-band connections, this disclosure contemplates any suitable in-band connections. Similarly, although this disclosure describes particular out-of-band connections, this disclosure contemplates any suitable out-of-band connections.

A server system 130 may provide services (such as web services) to client and other devices and systems. For example, a server system 130 may include one or more web servers, news servers, mail servers, message servers, advertising servers, file servers, application servers, exchange servers, database servers, proxy servers, other suitable servers, or a suitable combination thereof. A server system 130 may include hardware, software, or embedded logic components or a combination of two or more such components for carrying out the functions implemented or supported by server system 130. In addition, a server system 130 may include one or more servers and be a unitary server system or a distributed server system spanning multiple computer systems or multiple datacenters. Although this disclosure describes and illustrates particular server systems, this disclosure contemplates any suitable server systems.

Central controller 140 may act as a central controller for multi-hop wireless network 100, which may include coordinating ignition of DNs 160 and CNs 170, as described below. Central controller 140 may include hardware, software, or embedded logic components or a combination of two or more such components for carrying out its functions. In addition, central controller 140 may include one or more servers and be a unitary computer system or a distributed computer system spanning multiple computer systems or multiple datacenters. Central controller 140 may be connected to multi-hop wireless network 100 by network 120. In addition or as an alternative, central controller 140 may where appropriate connect to one or more network nodes of multi-hop wireless network 100 directly, for example, through out-of-band signaling by 2G, 3G, or 4G mobile telecommunications. Communication between central controller 140 and a network node of multi-hop through network 120 may be referred to as in-band. Although this disclosure describes and illustrates a particular central controller 140, this disclosure contemplates any suitable central controller 140.

In the example of FIG. 1, multi-hop wireless network 100 includes multiple DNs 160 and CNs 170. A DN 160 wirelessly communicates with one or more CNs 170 or one or more other DNs 160 to relay data through multi-hop wireless network 100. DN 160A also communicates through a link 150 with one or more edge devices of network 120 to connect multi-hop wireless network 100 to network 120, providing a point-of-presence (PoP) for multi-hop wireless network 100 on network 120. A CN 170 communicates with one or more DNs 160 and CE 110 to connect a customer network to the multi-hop wireless network. One or more wireline or other suitable links may connect a CN 170 to CE 110. A CE 100 may be part of a customer network located for example at a customer premises and may include one or more Wi-Fi APs, cellular base stations (such as femtocells), and related equipment or other CEs providing wireless or wired connectivity to one or more client devices. A client device may be an electronic device including hardware, software, or embedded logic components or a combination of two or more such components designed to carry out particular functions implemented or supported by the client device. For example, a client device may be a desktop or laptop computer, tablet, e-book reader, GPS device, camera, mobile telephone, appliance, augmented-reality or virtual-reality device, another suitable client device, or a suitable combination thereof. This disclosure contemplates any suitable client devices.

As described above, multi-hop wireless network 100 includes multiple DNs 160 and CNs 170. Wireless communication in multi-hop wireless network 100 may be point-to-point, and DNs 160 and CNs 170 may communicate wirelessly with each other in one or more frequency bands at or around 60 GHz. A DN 160 or CN 170 may have a maximum range of approximately 1.5 kilometers, but may typically communicate with other DNs 160 or CNs within approximately 200-300 meters. All or some of DNs 160 and CNs 170 the network nodes may be at fixed locations. For example, all or some of DNs 160 and CNs 170 may be affixed to street lamps, utility poles, other street furniture, or building exteriors.

A network node of multi-hop wireless network 100 may include one or more antenna arrays that are each capable of beamforming to direct signal transmission or reception by network node. A single antenna array capable of beamforming may be referred to as a sector. If a network node has multiple sectors, they will likely face different directions. For example, a network node affixed to a street pole could have four separate antenna arrays on it, with one facing north, one facing east, one facing south, and one facing west. To aim a sector for transmission or reception, the beamforming weight of the antenna array constituting the sector may be adjusted. A micro-route is a gross reflection or line of site between two sectors. A nano-route is a fine reflection or line of site between two sectors. Typically, a micro-route between two sectors has several possible nano-routes. Some of those nano-routes will provide better link capacity between the two sectors, and some of those nano-routes will interfere more with neighboring nodes. In the example of FIG. 1, the directions of the sectors of DNs 160 and CNs 170 for transmission and reception are shown as lobes with dashed lines. Each of these lobes represents a sector's main lobe (e.g. the direction of the greatest transmission power or reception sensitivity). A sector may also have side lobes and nulls, which are not shown in FIG. 1. In the example of FIG. 1, DN 160A has sectors aimed at DN 160B, DN 160D, and DN 160G; DN 160B has sectors aimed at DN 160A, DN 160C, and CN 170A; DN 160C has sectors aimed at DN 160B, DN 160D, and CN 170B; DN 160D has sectors aimed at DN 160A, DN 160C, DN 160E, and CN 170C; DN 160E has sectors aimed at DN 160D, DN 160F, DN 160G, and CN 170D; DN 160F has sectors aimed at DN 160E and DN 160G; DN 160G has sectors aimed at DN 160A, DN 160E, and DN 160F; CN 170A has a sector aimed at DN 160B; CN 170B has a sector aimed at DN 160C; CN 170C has a sector aimed at DN 160D; and CN 170D has a sector aimed at DN 160E. As described below, the sectors of DNs 160 and CNs 170 may be dynamically re-directed by changing the beamforming weights of the respective antenna arrays. Moreover, as further described below, the sectors of particular DNs 160 and CNs 170 may be dynamically re-directed in response to particular events. Although this disclosure describes and illustrates a particular example multi-hop wireless network with a particular number of particular network nodes in a particular arrangement with particular numbers of particular beamforming antenna arrays aimed in particular directions, this disclosure contemplates any suitable multi-hop wireless network with any suitable number of any suitable network nodes in any suitable arrangement with any suitable numbers of any suitable beamforming antenna arrays aimed in any suitable directions.

Figure 2:
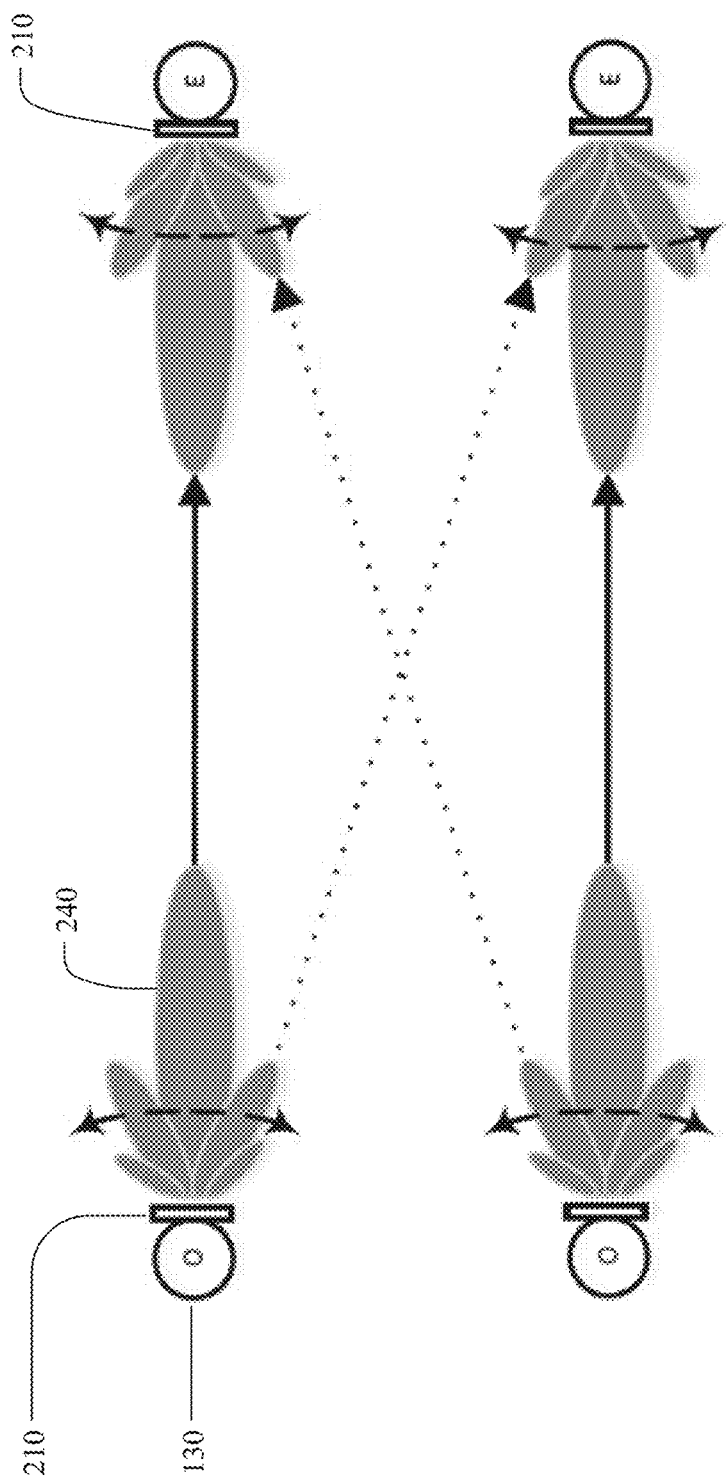
FIG. 2 illustrates example beamforming.

FIG. 2 illustrates example beamforming. In the example of FIG. 2, each network node 120 (which may be a DN 160 or a CN 170) includes a sector 220. Each sector 210 includes an array of beamforming antennas. To aim sector 220 for transmission, a processor in a network node 210 may instruct a beamformer in network node 120 to selectively weight or delay signals transmitted by the antennas of the sector 220 to aim main lobe 240 of the transmission in a desired direction. In addition to transmitting in the direction of main lobe 240, sector 220 may also transmit weaker signals in the directions of side lobes 260 and 280, which may interfere with other transmissions, as shown by the dotted directional lines in FIG. 2. To aim sector 220 for reception, a processor in network 210 may weigh, delay, or sum signals received by the antennas of sector 220.

Figure 3:
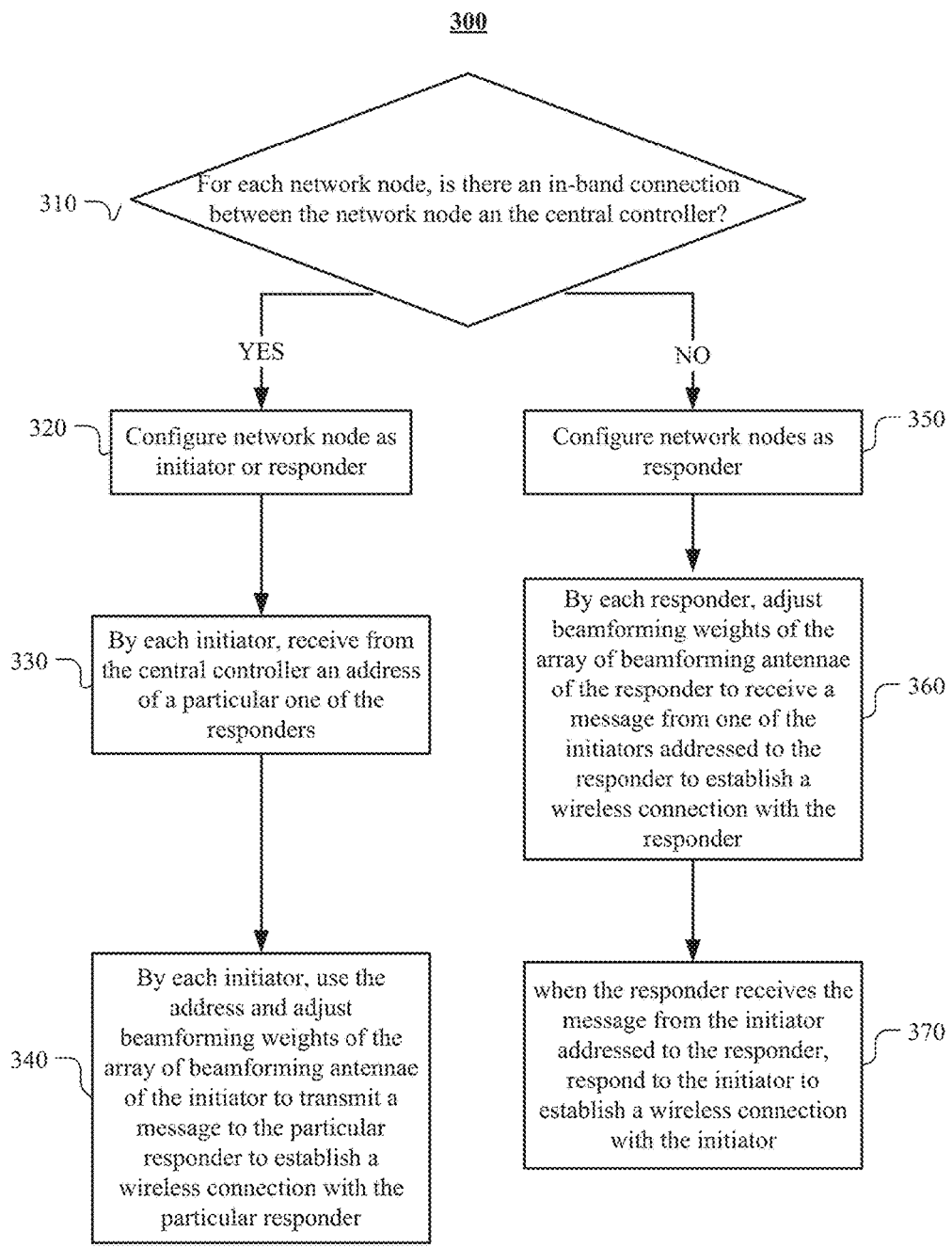
FIG. 3 illustrates an example method for igniting network nodes in a multi-hop wireless network.

FIG. 3 illustrates an example method for igniting network nodes in a multi-hop wireless network. The method may begin at step 310, where central controller 140 determines whether an in-band connection exists between a given network node and central controller 140. If an in-band connection exists, the method proceeds to step 320, where the given network node may be configured as an initiator. If no in-band connection exists, the method proceeds to step 350, where the given network node may be configured as a responder. At step 330, the initiator may receive from the central controller an address of a particular one of the responders. The address may include a MAC address of one of the responders. At step 340, the initiator may use the address and adjust beamforming weights of the array of beamforming antennae of the initiator to transmit a message to the particular responder to establish a wireless connection with the particular responder. Again, if no in-band connection exists between a given network node and the central controller 140, the given network node may be configured as a responder. This may be an automatic configuration that occurs after the expiration of a timer if no in-band connection has been established. This configuration occurs at step 350. At step 360, each responder may adjust beamforming weights of the array of beamforming antennae of the responder to receive a message from one of the initiators addressed to the responder to establish a wireless connection with the responder. At step 370, when the responder receives the message from the initiator addressed to the responder, it may respond to the initiator to establish a wireless connection with the initiator. Although this disclosure describes and illustrates particular steps of the method of FIG. 3 as occurring in a particular order, this disclosure contemplates any suitable steps of the method of FIG. 3 occurring in any suitable order. Moreover, although this disclosure describes and illustrates an example method for generating and sending tag candidates to a client system including the particular steps of the method of FIG. 3, this disclosure contemplates any suitable method for generating and sending tag candidates to a client system including any suitable steps, which may include all, some, or none of the steps of the method of FIG. 3, where appropriate. Furthermore, although this disclosure describes and illustrates particular components, devices, or systems carrying out particular steps of the method of FIG. 3, this disclosure contemplates any suitable combination of any suitable components, devices, or systems carrying out any suitable steps of the method of FIG. 3.

Figure 4:
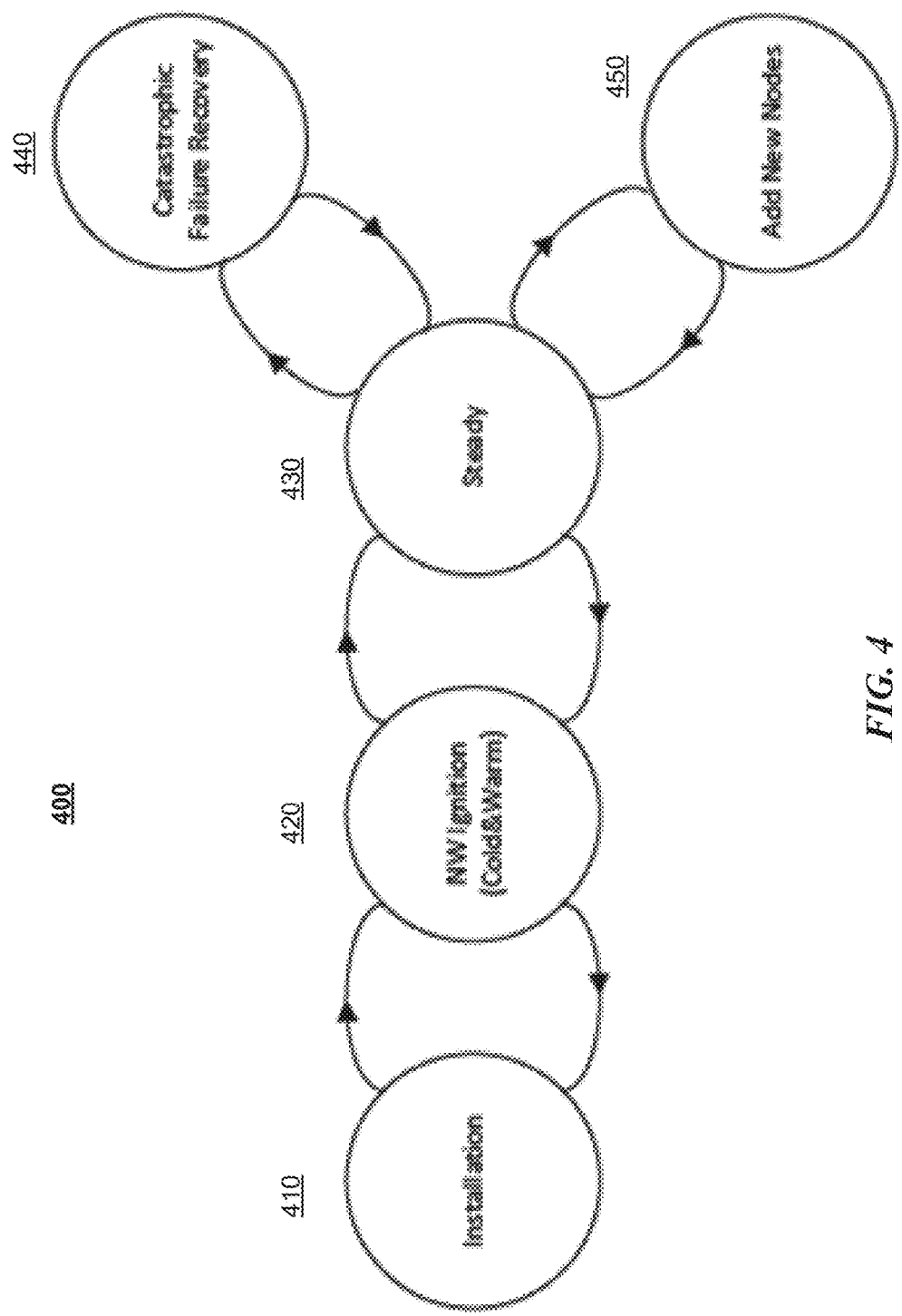
FIG. 4 illustrates example states of a multi-hop wireless network.

FIG. 4 illustrates example states of a multi-hop wireless network. At state 410, the multi-hop wireless network may undergo the initial installation stage. Installation may occur by physically placing one or more network nodes in planned deployment locations (e.g. on particular lamp posts, buildings, or dedicated utility poles). Alternatively, the network nodes may be placed in unplanned locations, in an arbitrary or random manner. Once the network nodes are physically in place, the devices may be powered on and data may be loaded onto each network node's memory. Alternatively, data may be loaded onto the network nodes' memories prior to physical placement. Loaded data may include firmware, location parameters, and specific beamforming parameters. As an example and not by way of limitation, it may be desired that two network nodes, NN1 and NN2, form a wireless connection between their respective sectors. The network nodes may include one or more sectors comprising one or more antenna arrays that link NN1 to NN2 via a wireless connection. These antenna arrays may require specific beamforming weight calibrations to achieve a connection. Such beamforming weight calibrations and related data may include GPS location, frequency, timing, and phase sync. These beamforming weight calibrations may be predetermined and loaded into NN1 and NN2 at any time before or after physical placement. After NN1 and NN2 are powered on, the stored beamforming weight calibration settings may be used during the ignition procedure at state 420 so that NN1 and NN2 may direct their antenna arrays according to the stored beamform weight calibration settings to achieve a wireless connection with each other.

After installation but before ignition at state 420, the central controller or other computing device may determine whether an in-band connection exists between the central controller and a particular network node. The particular network node may be a distribution node 133 or customer node 134. If an in-band connection exists, the central controller may configure the network node as either an initiator or a responder. If no in-band connection exists, the network node may be configured as a responder. An initiator may be understood to mean a network node that initially sends out a transmit signal to a particular other network node that has been configured as a responder. A responder may be understood to mean a network node that initially sends out a receive signal. In particular embodiments, one or more network nodes may configure themselves as responders without communicating with the central controller. The transmit and receive signals, respectively sent by an initiator and responder, may be adjusted directionally and/or through time to locate their respective counter-signal. As an example and not by way of limitation, if NN1 is configured as an initiator and NN2 is configured as a responder, NN1 may send out a transmit signal with NN2's unique address (e.g. MAC address). At the same time, NN2 may send out a receive signal in search of a transmit signal containing its own address. These signals may be adjusted left to right and up and down until they align with each other and a wireless connection is established.

At state 420, the network may be ignited. Network ignition may be understood to mean establishing wireless connection between the network nodes. In other words, a network node may be considered to be ignited if it has a wireless connection with another network node. Ignition may occur via an ignition procedure. The central controller may trigger the ignition procedure for a particular initiator. The ignition procedure may include a beamforming acquisition procedure, in which both the initiator and responder adjust their beamforming weights until a wireless connection is established. Alternatively, only one of the initiator or responder may adjust its beamforming weights, while the other holds its beamforming weights constant, until a wireless connection is established. The central ignition controller or some other computing device may have a database of beamforming pairs (e.g. a list of pairs of network nodes that have been predetermined to establish a wireless connection). For a given beamforming pair, the initiator may receive the MAC address of the responder. The initiator may scan for a "target responder" (e.g. a responder with a particular MAC address) by adjusting its beamforming weights. Simultaneously, the responder may adjust its beamforming weights to scan for a message that contains the responder's MAC address. If the responder detects a message that is addressed to the responder, it may send a signal back to the initiator acknowledging receipt of the transmitted signal in order to establish a wireless connection. This process may assure that other network nodes configured as responders do not respond to the initiator and create multi-access interference.

There may exist situations where a responder does not respond to the initiator within a predefined amount of time. Such situations may include cases where the responder is malfunctioning, the signal from the initiator is defective, or weather or other external forces inhibit a response signal to be sent. If the target responder does not respond to the initiator before a predefined amount of time has expired, the initiator may set its recipient address as the broadcast MAC address. This may trigger a broadcast signal to be sent to any responder in the network. The broadcast message may signal for any responder that has not yet been ignited to respond to the broadcast message. When a responder responds to the broadcast message, a wireless connection may be established between the initiator that sent the broadcast message and the responder that responded to the broadcast message. Upon successful ignition, the responder may be associated to the data link layer (layer 2).

At state 430, the network may be in the steady state. At this state, all the network nodes may be ignited and the network may be functioning as planned. During the steady state, the central controller or other computing device may record, for each of the network nodes, the beamforming weights of each array of antennae on each of the sectors. These beamforming weights and other statistics may be recorded and stored for use in future ignitions of the network nodes. At state 440, one or more of the network nodes may have entered catastrophic failure. This generally means that one or more of the network nodes has unexpectedly failed. Failure may result from a variety of reasons, such as weather or external forces may damaging one or more network nodes, internal defects may have caused one or more nodes to stop working, and so on. Such a failure may result in a disconnection of a wireless link. When this occurs, it may be necessary to perform maintenance on the network nodes and/or provide software updates to the network nodes. After the network nodes are repaired, the network nodes may be ready to be re-ignited. The central controller or other computing device may use the data and statistics that were recorded and stored during the previous steady state to speed up the ignition procedure of the network nodes. At state 450, one or more new network nodes may be added to the multi-hop wireless network. The process for adding new network nodes may be similar to the process discussed above for installing and igniting network nodes in the multi-hop network.

Figure 5:
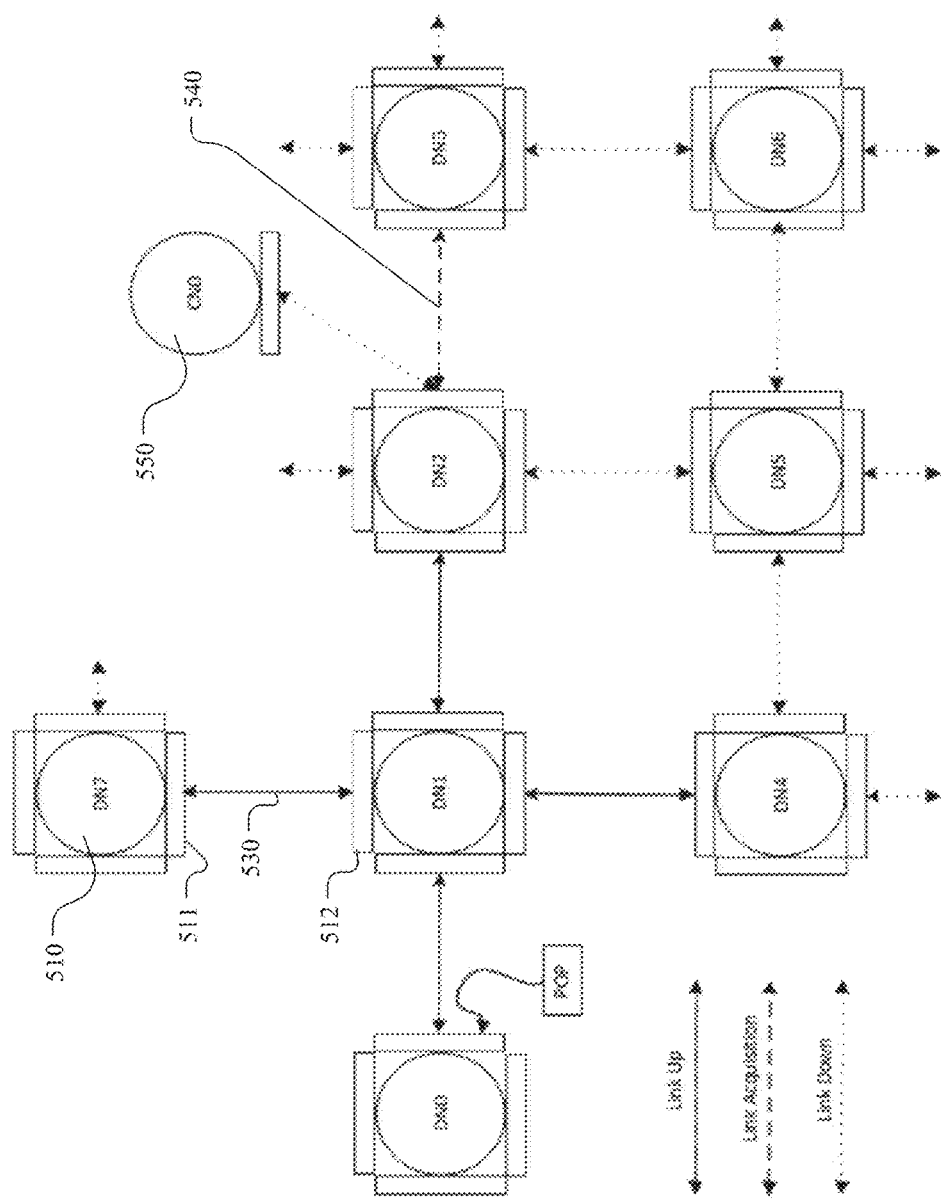
FIG. 5 illustrates example network nodes, sectors, and links in a multi-hop wireless network.

FIG. 5 illustrates example network nodes, sectors, and links in a multi-hop wireless network. Each sector may form a link (e.g. wireless connection) with another sector on a different network node. Illustrated are several distribution nodes 510 and a customer node 550. Each distribution node 510 and client node 550 may have one or more sectors 520. Each sector may include one or more beamforming antennas to form an array of beamforming antennae. As an example and not by way of limitation, if the distribution node labeled DN7 is configured to form a link with DN1, the array of beamforming antennae located in sector 520, may form a link with the array of beamforming antennae located in sector 512. This link may be formed using the method described herein. Link acquisition 540 may illustrate that DN2 and DN3 are in the process of establishing a link. The beamforming antenna arrays on DN2 and DN3 may still be scanning and/or adjusting their beamforming weights until the desired wireless connection is established.

Figure 6:
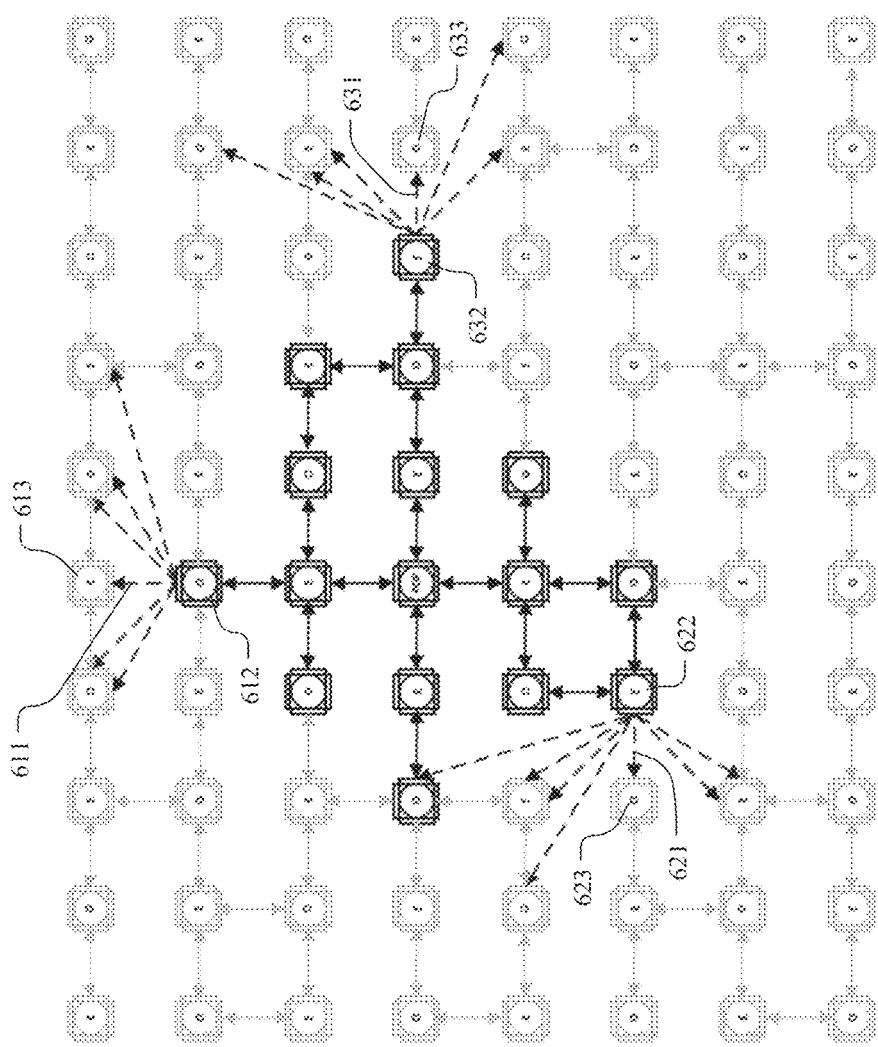
FIG. 6 illustrates example parallel ignition of network nodes in a multi-hop wireless network.

FIG. 6 illustrates example parallel ignition of network nodes in a multi-hop wireless network. Initiators 612, 622, and 632 may simultaneously send messages to many different responders. The messages may each contain an address (e.g. MAC address) for a particular responder. Responders 613, 623, and 633 may be the responders with an address matching the respective messages. Thus, links 611, 621, and 631 may be established between initiators 612, 622, and 632 and responders 613, 623, and 633. In this way, multiple network nodes may be ignited in parallel.

In particular embodiments, ignition of one or more network nodes is executed in conjunction with installation of at least some of the network nodes of the multi-hop wireless network. There are three main options for installing and igniting the network nodes in the multi-hop wireless network. First, all the network nodes may be installed, followed by all the network nodes being ignited. Second, installation and ignition may be performed on a link by link basis. This may be accomplished by installing the network nodes one at a time, and igniting each upon installment. If ignition fails for a particular network node, the position and orientation of the network node may be adjusted manually or automatically and ignition may be re-tried. The third option may be to combine the first two options to install and ignite a plurality, or subset, of network nodes, as is illustrated in FIG. 6.

In particular embodiments, ignition of at least a subset of the network nodes of the multi-hop wireless network may be executed after the subset has operated in steady state for a period of time, and the ignition may be based on operational parameters of the network nodes in the subset during the period of time and statistics about the steady-state operation of the subset collected during the period of time. This ignition based on information and statistics learned during a prior steady state operation may be referred to as "warm start." As an example and not by way of limitation, a multi-hop wireless network may be operating in the steady state for a period of time, during which time statistics and information about the operational parameters of at least a subset of the network nodes may be gathered and recorded. The operational parameters may include information and statistics such as beamforming weight settings, location, orientation, and so on. After the subset of network nodes has operated in the steady state for a period of time, at least a subset of the network may need to go back to the ignition state 420 for various reasons. As an example and not by way of limitation, a power outage may create a reset to at least some of the network nodes. To save time and speed up re-ignition, the central controller or other computing device may use the recorded operational parameters gathered from the steady state to more quickly orient the network nodes and/or adjust the beamforming weights of the array of antennae on the network nodes. The central controller may inform individual network node devices about their steady state information so that the network node devices may resume their steady state operation when they are powered on again. Alternatively, each network node may store its own operational parameters (e.g. information and statistics about beamforming weights settings, calibrations, orientations, etc.) about its steady state operation. In this way, at least a portion of the network nodes may be ignited in parallel by defaulting to the orientations and beamforming weights their last known steady state. This may be especially true if the power outage was for a relatively short period of time (e.g. the network nodes were without power for seconds, minutes, or hours).

There may be situations where at least a subset of network nodes on a multi-hop wireless network undergoes a planned reset and re-ignition. This planned re-ignition process may be referred to as "hot start." As an example and not by way of limitation, the firmware on one or more network nodes may need to be upgraded. Thus, the nodes requiring the firmware update may download the new firmware image from a network management system or other suitable computing device. Once the download is complete, the central controller or other computing device may inform each node to perform a power cycle at a scheduled time in the future. If only a portion of the network nodes need the firmware upgrade, network nodes adjoining those that are being upgraded may be informed to re-route traffic and/or plan for a reboot of the upgraded network nodes. After a network node has been power cycled, it may wait a pre-defined period of time before starting the ignition procedure as either an initiator or responder, as discussed herein. The wait time may be necessary to allow all the network nodes to power up successfully before network ignition begins. Upon the start of the ignition process, each network node may use the operational parameters stored during the previous steady state operation to establish one or more links with one or more other network nodes.

Figure 7:
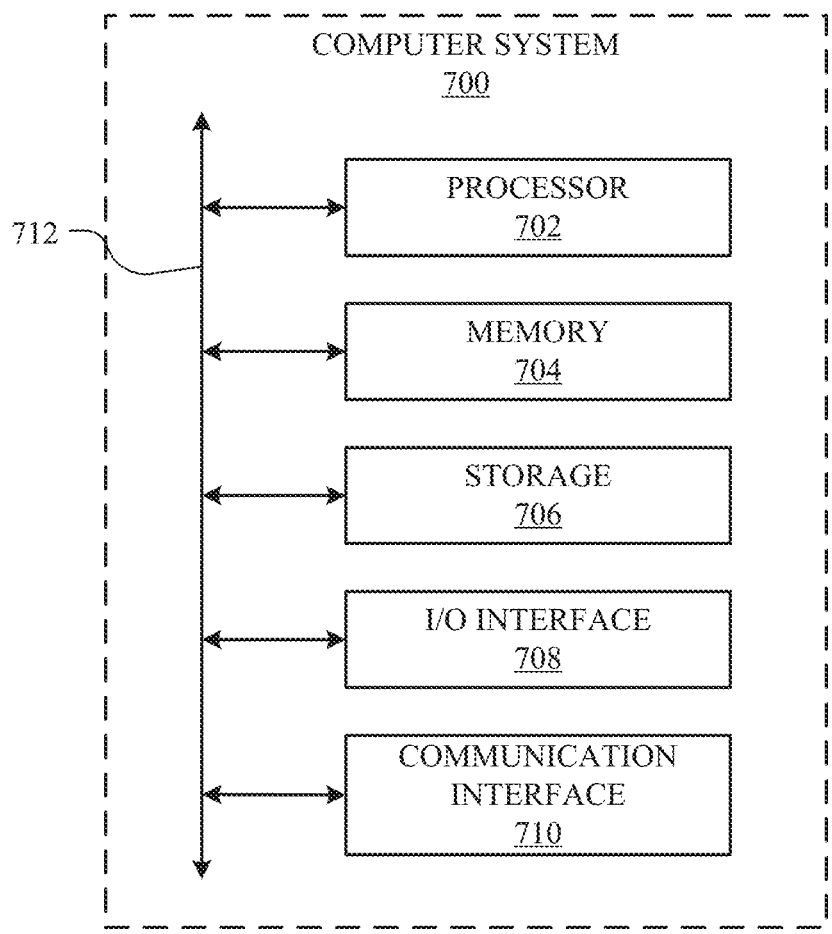
FIG. 7 illustrates an example computer system.

FIG. 7 illustrates an example computer system 700. In particular embodiments, one or more computer systems 700 perform one or more steps of one or more methods described or illustrated herein. In particular embodiments, one or more computer systems 700 provide functionality described or illustrated herein. In particular embodiments, software running on one or more computer systems 700 performs one or more steps of one or more methods described or illustrated herein or provides functionality described or illustrated herein. Particular embodiments include one or more portions of one or more computer systems 700. Herein, reference to a computer system may encompass a computing device, and vice versa, where appropriate. Moreover, reference to a computer system may encompass one or more computer systems, where appropriate.

This disclosure contemplates any suitable number of computer systems 700. This disclosure contemplates computer system 700 taking any suitable physical form. As example and not by way of limitation, computer system 700 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 700 may include one or more computer systems 700; be unitary or distributed; span multiple locations; span multiple machines; span multiple data centers; or reside in a cloud, which may include one or more cloud components in one or more networks. Where appropriate, one or more computer systems 700 may perform without substantial spatial or temporal limitation one or more steps of one or more methods described or illustrated herein. As an example and not by way of limitation, one or more computer systems 700 may perform in real time or in batch mode one or more steps of one or more methods described or illustrated herein. One or more computer systems 700 may perform at different times or at different locations one or more steps of one or more methods described or illustrated herein, where appropriate.

In particular embodiments, computer system 700 includes a processor 702, memory 704, storage 706, an input/output (I/O) interface 708, a communication interface 710, and a bus 712. Although this disclosure describes and illustrates a particular computer system having a particular number of particular components in a particular arrangement, this disclosure contemplates any suitable computer system having any suitable number of any suitable components in any suitable arrangement.

In particular embodiments, processor 702 includes hardware for executing instructions, such as those making up a computer program. As an example and not by way of limitation, to execute instructions, processor 702 may retrieve (or fetch) the instructions from an internal register, an internal cache, memory 704, or storage 706; decode and execute them; and then write one or more results to an internal register, an internal cache, memory 704, or storage 706. In particular embodiments, processor 702 may include one or more internal caches for data, instructions, or addresses. This disclosure contemplates processor 702 including any suitable number of any suitable internal caches, where appropriate. As an example and not by way of limitation, processor 702 may include one or more instruction caches, one or more data caches, and one or more translation lookaside buffers (TLBs). Instructions in the instruction caches may be copies of instructions in memory 704 or storage 706, and the instruction caches may speed up retrieval of those instructions by processor 702. Data in the data caches may be copies of data in memory 704 or storage 706 for instructions executing at processor 702 to operate on; the results of previous instructions executed at processor 702 for access by subsequent instructions executing at processor 702 or for writing to memory 704 or storage 706; or other suitable data. The data caches may speed up read or write operations by processor 702. The TLBs may speed up virtual-address translation for processor 702. In particular embodiments, processor 702 may include one or more internal registers for data, instructions, or addresses. This disclosure contemplates processor 702 including any suitable number of any suitable internal registers, where appropriate. Where appropriate, processor 702 may include one or more arithmetic logic units (ALUs); be a multi-core processor; or include one or more processors 702. Although this disclosure describes and illustrates a particular processor, this disclosure contemplates any suitable processor.

In particular embodiments, memory 704 includes main memory for storing instructions for processor 702 to execute or data for processor 702 to operate on. As an example and not by way of limitation, computer system 700 may load instructions from storage 706 or another source (such as, for example, another computer system 700) to memory 704. Processor 702 may then load the instructions from memory 704 to an internal register or internal cache. To execute the instructions, processor 702 may retrieve the instructions from the internal register or internal cache and decode them. During or after execution of the instructions, processor 702 may write one or more results (which may be intermediate or final results) to the internal register or internal cache. Processor 702 may then write one or more of those results to memory 704. In particular embodiments, processor 702 executes only instructions in one or more internal registers or internal caches or in memory 704 (as opposed to storage 706 or elsewhere) and operates only on data in one or more internal registers or internal caches or in memory 704 (as opposed to storage 706 or elsewhere). One or more memory buses (which may each include an address bus and a data bus) may couple processor 702 to memory 704. Bus 712 may include one or more memory buses, as described below. In particular embodiments, one or more memory management units (MMUs) reside between processor 702 and memory 704 and facilitate accesses to memory 704 requested by processor 702. In particular embodiments, memory 704 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 704 may include one or more memories 704, where appropriate. Although this disclosure describes and illustrates particular memory, this disclosure contemplates any suitable memory.

In particular embodiments, storage 706 includes mass storage for data or instructions. As an example and not by way of limitation, storage 706 may include a hard disk drive (HDD), a floppy disk drive, flash memory, an optical disc, a magneto-optical disc, magnetic tape, or a Universal Serial Bus (USB) drive or a combination of two or more of these. Storage 706 may include removable or non-removable (or fixed) media, where appropriate. Storage 706 may be internal or external to computer system 700, where appropriate. In particular embodiments, storage 706 is non-volatile, solid-state memory. In particular embodiments, storage 706 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 706 taking any suitable physical form. Storage 706 may include one or more storage control units facilitating communication between processor 702 and storage 706, where appropriate. Where appropriate, storage 706 may include one or more storages 706. Although this disclosure describes and illustrates particular storage, this disclosure contemplates any suitable storage.

In particular embodiments, I/O interface 708 includes hardware, software, or both, providing one or more interfaces for communication between computer system 700 and one or more I/O devices. Computer system 700 may include one or more of these I/O devices, where appropriate. One or more of these I/O devices may enable communication between a person and computer system 700. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 708 for them. Where appropriate, I/O interface 708 may include one or more device or software drivers enabling processor 702 to drive one or more of these I/O devices. I/O interface 708 may include one or more I/O interfaces 708, where appropriate. Although this disclosure describes and illustrates a particular I/O interface, this disclosure contemplates any suitable I/O interface.

In particular embodiments, communication interface 710 includes hardware, software, or both providing one or more interfaces for communication (such as, for example, packet-based communication) between computer system 700 and one or more other computer systems 700 or one or more networks. As an example and not by way of limitation, communication interface 710 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 710 for it. As an example and not by way of limitation, computer system 700 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 700 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 700 may include any suitable communication interface 710 for any of these networks, where appropriate. Communication interface 710 may include one or more communication interfaces 710, where appropriate. Although this disclosure describes and illustrates a particular communication interface, this disclosure contemplates any suitable communication interface.

In particular embodiments, bus 712 includes hardware, software, or both coupling components of computer system 700 to each other. As an example and not by way of limitation, bus 712 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 712 may include one or more buses 712, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method comprising:
by each of one or more network nodes of a multi-hop wireless network that are configured as initiators:
receiving from a central controller of the multi-hop wireless network an address of a particular network node of the multi-hop wireless network that is configured as a responder, wherein each network node of the multi-hop wireless network comprises at least one array of beamforming antennae;
using the address and by adjusting beamforming weights of the array of beamforming antennae of the initiator, transmitting a message to establish a wireless connection with the particular network node configured as a responder; and
when the initiator does not receive a response from the particular responder within a predetermined amount of time, using a broadcast address and by adjusting beamforming weights of the array of beamforming antennae of the initiator, transmitting a message to establish a wireless connection with a responder that has not already established a wireless connection with another initiator.

2. The method of claim 1, wherein one or more of the network nodes configure themselves as responders without communicating with the central controller.

3. The method of claim 1, wherein one or more of the network nodes are configured as responders by the central controller.

4. The method of claim 1, wherein fewer than all the network nodes with in-band connections to the central controller are configured as initiators.

5. The method of claim 1, wherein the addresses are Media Access Control (MAC) addresses.

6. The method of claim 1, wherein one or more of the network nodes each comprises a plurality of arrays of beamforming antennae that are each operable to support a wireless connection between the network node and another one of the network nodes.

7. The method of claim 1, wherein, the method is executed in conjunction with installation of at least some of the network nodes of the multi-hop wireless network.

8. The method of claim 1, wherein the method is executed for at least a subset of the network nodes of the multi-hop wireless network after the subset has operated in steady state for a period of time and based on one or more operational parameter states of the network nodes in the subset during the period of time and statistics about the steady-state operation of the subset collected during the period of time.

9. The method of claim 1, wherein each of one or more of the network nodes is configured as an initiator by the central controller.

10. The method of claim 1, wherein:
each of one or more of the network nodes is configured as an initiator by an installer of one or more portions of the multi-hop wireless network; and
each of one or more of the network nodes is configured as a responder by the installer.

11. The method of claim 1, further comprising, by the responder that has not already established a wireless connection with another initiator:
adjusting beamforming weights of the array of beamforming antennae of the responder to receive a message from one of the initiators addressed to the responder to establish a wireless connection with the responder; and
when the responder receives the message from the initiator addressed to the responder, responding to the initiator to establish a wireless connection with the initiator.

12. One or more computer-readable non-transitory storage media embodying software that is operable when executed to:
on each of one or more network nodes of a multi-hop wireless network that are configured as initiators:
receive from a central controller of a multi-hop wireless network an address of a particular network node of the multi-hop wireless network that is configured as a responder, wherein each network node of the multi-hop wireless network comprises at least one array of beamforming antennae;
using the address and by adjusting beamforming weights of the array of beamforming antennae of the initiator, transmit a message to establish a wireless connection with the particular network node configured as a responder; and when the initiator does not receive a response from the particular responder within a predetermined amount of time, using a broadcast address and by adjusting beamforming weights of the array of beamforming antennae of the initiator, transmitting a message to establish a wireless connection with a responder that has not already established a wireless connection with another initiator.

13. The media of claim 12, wherein one or more of the network nodes configure themselves as responders without communicating with the central controller.

14. The media of claim 12, wherein one or more of the network nodes are configured as responders by the central controller.

15. The media of claim 12, wherein fewer than all the network nodes with in-band connections to the central controller are configured as initiators.

16. The media of claim 12, wherein the software is further operable when executed to, on the responder that has not already established a wireless connection with another initiator:

adjust beamforming weights of the array of beamforming antennae of the responder to receive a message from one of the initiators addressed to the responder to establish a wireless connection with the responder; and when the responder receives the message from the initiator addressed to the responder, respond to the initiator to establish a wireless connection with the initiator.

17. A system comprising: one or more processors; and a memory coupled to the processors comprising instructions executable by the processors, the processors being operable when executing the instructions to:

on each of one or more network nodes of a multi-hop wireless network that are configured as initiators:

receive from a central controller of a multi-hop wireless network an address of a particular network node of the multi-hop wireless network that is configured as a responder, wherein each network node of the multi-hop wireless network comprises at least one array of beamforming antennae;

using the address and by adjusting beamforming weights of the array of beamforming antennae of the initiator, transmit a message to establish a wireless connection with the particular network node configured as a responder; and when the initiator does not receive a response from the particular responder within a predetermined amount of time, using a broadcast address and by adjusting beamforming weights of the array of beamforming antennae of the initiator, transmitting a message to establish a wireless connection with a responder that has not already established a wireless connection with another initiator.

18. The system of claim 17, wherein one or more of the network nodes configure themselves as responders without communicating with the central controller.

19. The system of claim 17, wherein one or more of the network nodes are configured as responders by the central controller.

* * * * *